(12) United States Patent
Baril et al.

(10) Patent No.: US 11,064,984 B2
(45) Date of Patent: Jul. 20, 2021

(54) SPECIMEN CONTAINMENT DEVICE

(71) Applicant: COVIDIEN LP, Mansfield, MA (US)

(72) Inventors: Jacob C. Baril, Norwalk, CT (US);
Saumya Banerjee, Hamden, CT (US);
Justin J. Thomas, New Haven, CT (US); Matthew A. Dinino, Newington, CT (US); Roy J. Pilletere, North Haven, CT (US); George S. Matta, Plainville, MA (US); Christopher M. Meehan, New Haven, CT (US); Amy L. Kung, Hamden, CT (US); Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 139 days.

(21) Appl. No.: 16/405,085

(22) Filed: May 7, 2019

(65) Prior Publication Data
US 2020/0352551 A1    Nov. 12, 2020

(51) Int. Cl.
*A61B 17/00*     (2006.01)

(52) U.S. Cl.
CPC ............ *A61B 17/00234* (2013.01); *A61B 2017/00287* (2013.01); *A61B 2017/00473* (2013.01); *A61B 2017/00867* (2013.01)

(58) Field of Classification Search
CPC .... A61B 17/00234; A61B 2017/00287; A61B 2017/00473; A61B 2017/00867; A61B 2017/0046; A61B 2017/2212; A61B 2017/22094; A61B 17/221; A61B 17/32056; A61B 17/26
USPC ........................................................ 606/114
See application file for complete search history.

(56) References Cited

U.S. PATENT DOCUMENTS

| | | | |
|---|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,927,427 A | 5/1990 | Kriauciunas et al. |

(Continued)

FOREIGN PATENT DOCUMENTS

| | | |
|---|---|---|
| DE | 3542667 A1 | 6/1986 |
| DE | 4204210 A1 | 8/1992 |

(Continued)

*Primary Examiner* — Kathleen S Holwerda
*Assistant Examiner* — Brooke Labranche
(74) *Attorney, Agent, or Firm* — Carter, DeLuca & Farrell LLP (57) ABSTRACT

A specimen containment device includes an actuation assembly, a bag assembly, a bag locking mechanism, and an articulation locking mechanism. The actuation assembly includes a handle assembly, an elongated member, a release rod, and a holding assembly. The bag locking mechanism is disposed in mechanical cooperation with the handle assembly and enables the actuation assembly to selectively retain the bag assembly. The articulation locking assembly is disposed in mechanical cooperation with the handle assembly and is configured to selectively lock the holding assembly in a first position where at least a portion of the holding assembly is disposed along a longitudinal axis defined by the elongated member.

16 Claims, 11 Drawing Sheets

(56) References Cited

U.S. PATENT DOCUMENTS

| | | |
|---|---|---|
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,405,360 A | 4/1995 | Tovey |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,578,048 A | 11/1996 | Pasqualucci et al. |
| 5,601,572 A | 2/1997 | Middleman et al. |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,720,754 A | 2/1998 | Middleman et al. |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,779,716 A | 7/1998 | Cano et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,621,923 B2 | 11/2009 | Goldenberg |
| 8,968,329 B2 | 3/2015 | Cabrera |
| 10,327,745 B2 | 6/2019 | Cabrera |
| 2004/0097960 A1 | 5/2004 | Terachi et al. |
| 2004/0133213 A1 | 7/2004 | Bagley et al. |
| 2004/0138587 A1 | 7/2004 | Lyons |
| 2004/0243173 A1 | 12/2004 | Inoue |
| 2005/0267492 A1 | 12/2005 | Poncet et al. |
| 2006/0052799 A1 | 3/2006 | Middleman et al. |
| 2006/0058776 A1 | 3/2006 | Bilsbury |
| 2006/0200169 A1 | 9/2006 | Sniffin |
| 2006/0200170 A1 | 9/2006 | Aranyi |
| 2006/0212040 A1 | 9/2006 | Goldstein |
| 2006/0229639 A1 | 10/2006 | Whitfield |
| 2006/0229640 A1 | 10/2006 | Whitfield |
| 2006/0293697 A1 | 12/2006 | Nakao et al. |
| 2007/0016224 A1 | 1/2007 | Nakao |
| 2007/0016225 A1 | 1/2007 | Nakao |
| 2007/0073251 A1 | 3/2007 | Zhou |
| 2007/0088370 A1 | 4/2007 | Kahle et al. |
| 2007/0106304 A1 | 5/2007 | Hammack et al. |
| 2007/0135780 A1 | 6/2007 | Pagedas |
| 2007/0135781 A1 | 6/2007 | Hart |
| 2008/0091215 A1 | 4/2008 | Saleh |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2009/0306683 A1 | 12/2009 | Zwolinski et al. |
| 2010/0000471 A1 | 1/2010 | Hibbard |
| 2010/0152746 A1 | 6/2010 | Ceniccola et al. |
| 2011/0184311 A1 | 7/2011 | Parihar et al. |
| 2011/0184430 A1 | 7/2011 | Parihar et al. |
| 2011/0184431 A1 | 7/2011 | Parihar et al. |
| 2011/0184432 A1 | 7/2011 | Parihar et al. |
| 2011/0184433 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |

(56) References Cited

U.S. PATENT DOCUMENTS

2011/0190781 A1    8/2011   Collier et al.
2011/0299799 A1   12/2011   Towe
2012/0179165 A1    7/2012   Grover

FOREIGN PATENT DOCUMENTS

| DE | 19624826 A1 | 1/1998 |
|----|-------------|--------|
| EP | 2184014 A2 | 5/2010 |
| EP | 2474270 A2 | 7/2012 |
| WO | 9315675 A1 | 8/1993 |
| WO | 9509666 A1 | 4/1995 |
| WO | 2004002334 A1 | 1/2004 |
| WO | 2005112783 A1 | 12/2005 |

SPECIMEN CONTAINMENT DEVICE

TECHNICAL FIELD

The present disclosure relates generally to a specimen containment device for use during a surgical procedure, and more particularly, the present disclosure relates to a specimen containment device including a bag and a device that deploys the bag.

BACKGROUND

Minimal invasive procedures may be used for partial or total removal of a body specimen, e.g., body tissue or organs, from an interior portion of a body cavity, e.g. nephrectomy, cholecystectomy, and other such procedures. During such procedures, it is common that a cyst, tumor, tissue, foreign object or organ must be contained or removed via the access opening in the skin, or through a cannula. Various types of containment or collection devices, for example, pouches or sacs, have been disclosed to facilitate this procedure.

In certain situations, it is often difficult to remove a pouch or sac through a small laparoscopic incision and/or cannula when, for instance, the specimen therein is relatively large or solid which would make the pouch difficult to remove through a small opening, for example, a small incision and a cannula.

Accordingly, it may be useful to provide a specimen containment device with a deployable and/or releasable bag to help facilitate such removal of at least portions of the specimen containment device through a small opening.

SUMMARY

The present disclosure relates to a specimen containment device including an actuation assembly, a bag assembly, a bag locking mechanism, and an articulation locking assembly. The actuation assembly includes a handle assembly, an elongated member extending distally from the handle assembly and defining a longitudinal axis, a release rod extending distally from a portion of the handle assembly, and a holding assembly disposed distally of the elongated member. At least a portion of the holding assembly is movable from a first position where the at least a portion of the holding assembly is disposed along the longitudinal axis, to a second position where the at least a portion of the holding assembly is disposed at a non-parallel angle with respect to the longitudinal axis. The bag locking mechanism is disposed in mechanical cooperation with the handle assembly of the actuation assembly and is configured to enable the actuation assembly to selectively retain the bag assembly. The articulation locking assembly is disposed in mechanical cooperation with the handle assembly of the articulation assembly and is configured to selectively lock the holding assembly in the first position.

In aspects according to the present disclosure, the holding assembly includes a first arm and a second arm which are each disposed arcuately relative to the longitudinal axis. In yet other aspects, both of the first arm and the second arm are longitudinally translatable at least partially through the elongated member. In yet additional aspects, both the first arm and the second arm are made from a shape memory material.

In still other aspects, the handle assembly includes a proximal handle and a distal handle. The proximal handle is translatable along the longitudinal axis relative to the distal handle. In other aspects, a portion of the release rod is coupled to the proximal handle such that longitudinal translation of the proximal handle relative to the distal handle causes a corresponding longitudinal translation of the release rod.

In other aspects, the bag locking mechanism includes a proximal portion coupled to a proximal portion of the release rod and extends through a proximal handle of the handle assembly. In yet other aspects, the bag locking mechanism includes a distal portion coupled to a distal end of the release rod and is configured to selectively extend through an opening of a securing structure of the bag assembly. Additionally, the distal portion of the bag locking mechanism is disposed at a non-parallel angle relative to the longitudinal axis. In still other aspects, the distal portion of the bag locking mechanism is configured to selectively sit at least partially within a receptacle of the securing structure of the bag assembly. In further aspects, rotation of at least a portion of the bag locking mechanism about the longitudinal axis relative to the elongated member causes the distal portion of the bag locking mechanism to move from a first orientation where the distal portion of the bag locking mechanism is at least partially within the receptacle of the securing structure, to a second orientation where the distal portion of the bag locking mechanism is aligned with the opening of the securing structure.

In additional aspects, the articulation locking mechanism includes an articulation handle disposed proximally of the proximal handle of the handle assembly, an articulation rod engaged with a proximal portion of the holding assembly, and a link interconnecting the articulation handle and the articulation rod. In yet other aspects, the articulation handle is pivotally connected to the proximal handle of the handle assembly and is movable relative to the proximal handle between a first position where the articulation rod is longitudinally translatable relative to the elongated member, and a second position where the articulation rod is fixed from moving longitudinally relative to the elongated member. In still other aspects, when the articulation handle is in the first position, the link and the articulation rod form an angle in the range of about 100° to about 120°. In additional aspects, when the articulation handle is in the second position, the link and the articulation rod form an angle of at least 180°, e.g., from about 180° to about 220°.

In further aspects, the link is pinned to the articulation handle with a first pin, and the link is pinned to the articulation rod with a second pin.

Aspects of the present disclosure also relate to a specimen containment device including an actuation assembly, a bag assembly, and an articulation assembly. The actuation assembly includes a handle assembly, an elongated member extending distally from the handle assembly and defining a longitudinal axis, a release rod extending distally from a portion of the handle assembly, and a holding assembly disposed distally of the elongated member. At least a portion of the holding assembly is movable from a first position where the at least a portion of the holding assembly is disposed along the longitudinal axis, to a second position where the at least a portion of the holding assembly is disposed at a non-parallel angle with respect to the longitudinal axis. The bag assembly is selectively coupled to the actuation assembly. The articulation locking assembly is disposed in mechanical cooperation with the handle assembly of the articulation assembly and is configured to selectively lock the holding assembly in the first position. The articulation locking mechanism includes an articulation handle disposed proximally of a portion of the handle assembly, an articulation rod engaged with a proximal portion of the holding assembly, and a link interconnecting the articulation handle and the articulation rod. The articulation handle is pivotally connected to a portion of the handle assembly and is movable relative to the handle assembly between a first position where the articulation rod is longitudinally translatable relative to the elongated member, and a second position where the articulation rod is fixed from moving longitudinally relative to the elongated member.

In other aspects, when the articulation handle is in the first position, the link and the articulation rod form an angle in the range of about 100° to about 120°. In additional aspects, when the articulation handle is in the second position, the link and the articulation rod form an angle of at least 180°, e.g., from about 180° to about 220°.

BRIEF DESCRIPTION OF THE DRAWINGS

Various embodiments of the specimen containment device are described herein with reference to the drawings wherein.

DETAILED DESCRIPTION

Embodiments of the presently disclosed specimen containment devices are described in detail with reference to the drawings, in which like reference numerals designate identical or corresponding elements in each of the several views. As used herein the term "distal" refers to that portion of the device is farther from the user, while the term "proximal" refers to that portion of the device that is closer to the user.

Figure 1A:
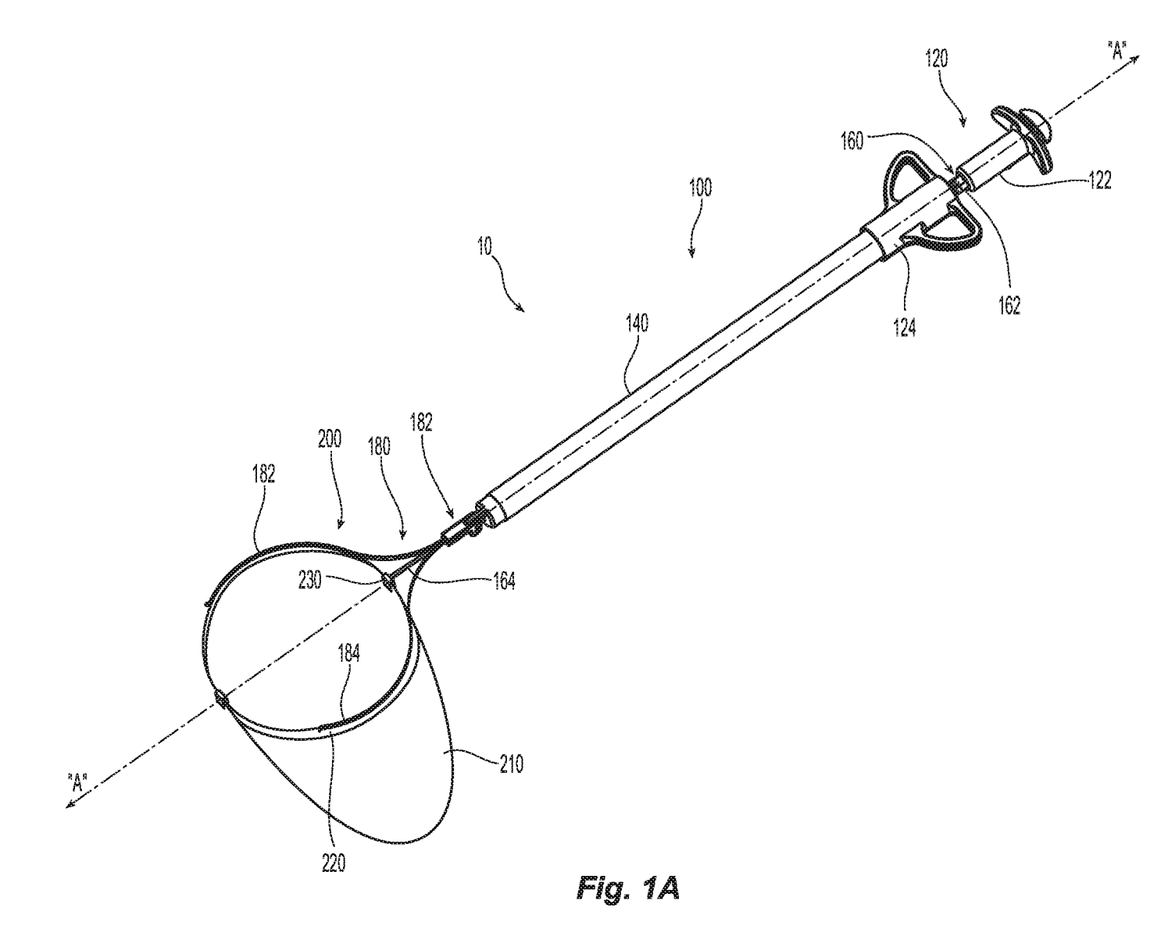
FIG. 1A is a perspective view of a specimen containment device in accordance with embodiments of the present disclosure.
Figure 1B:
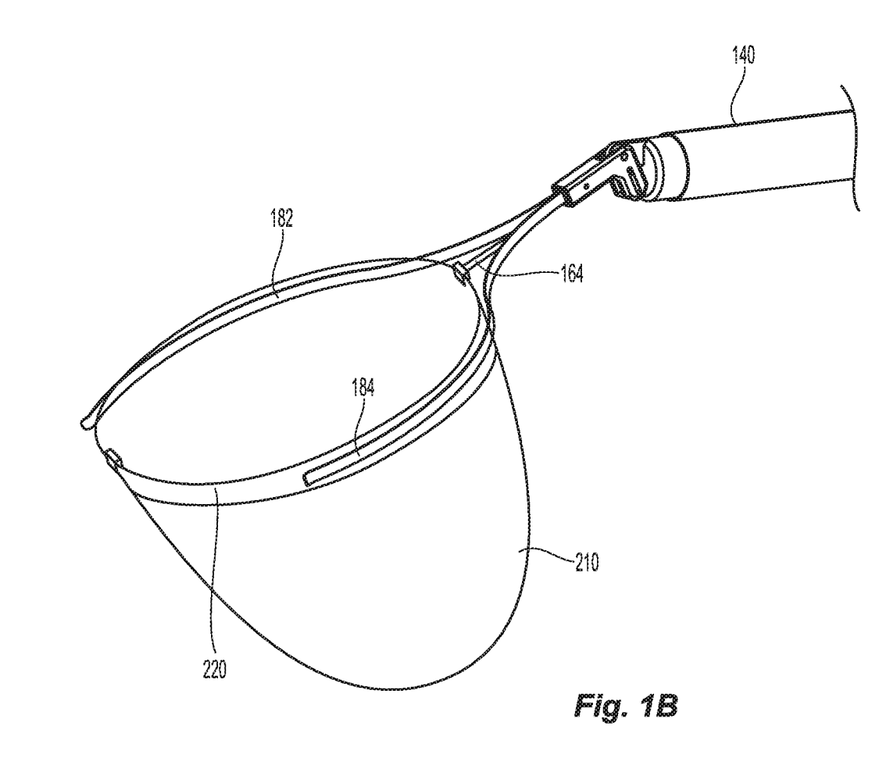
FIG. 1B is a perspective view of a distal portion of the specimen containment device of FIG. 1A shown in an articulated position.
Figure 2:
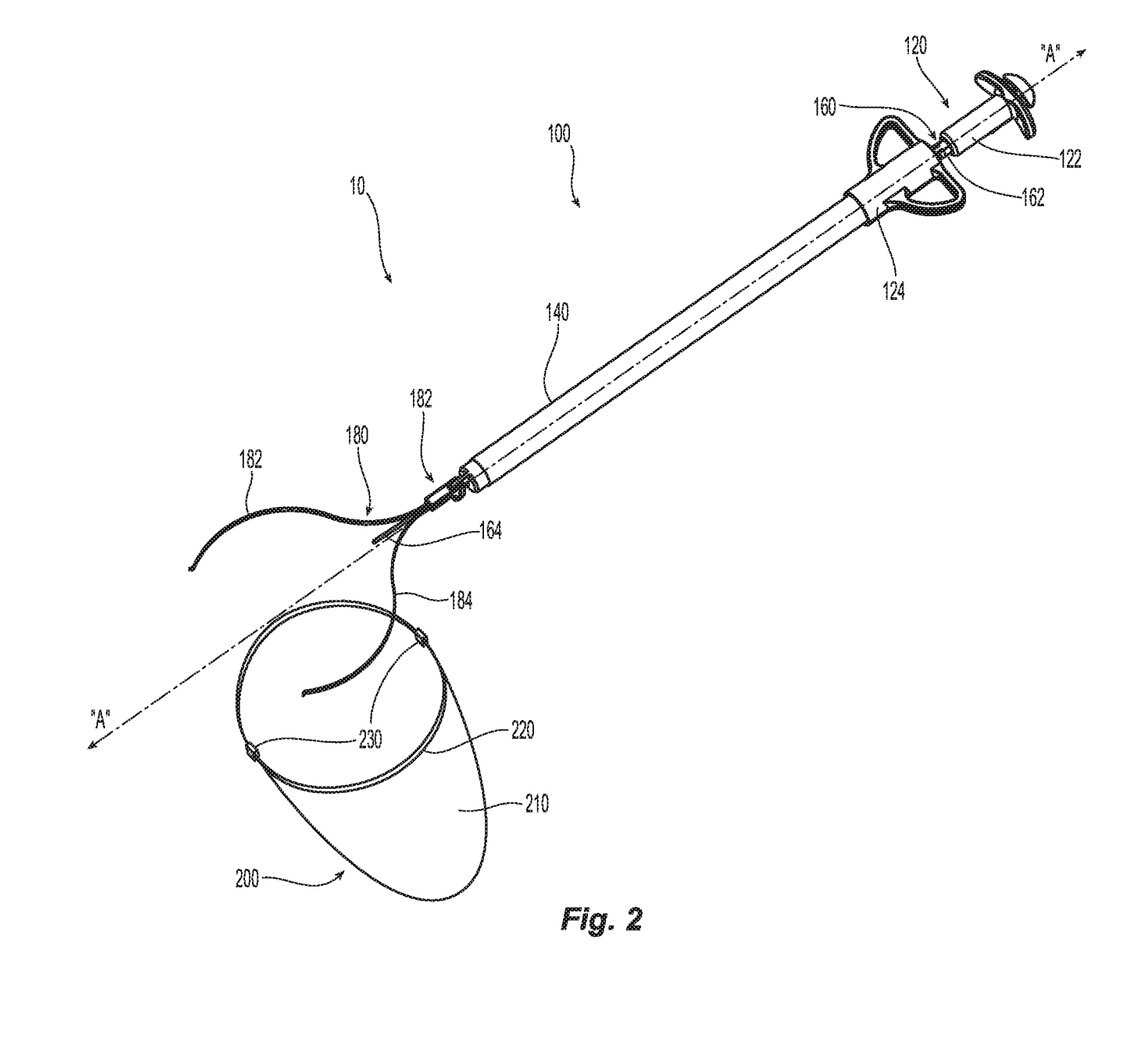
FIG. 2 is a perspective view of the specimen containment device of FIG. 1 illustrating a bag assembly of the specimen containment device separated from an actuation assembly of the specimen containment device.
Figure 3:
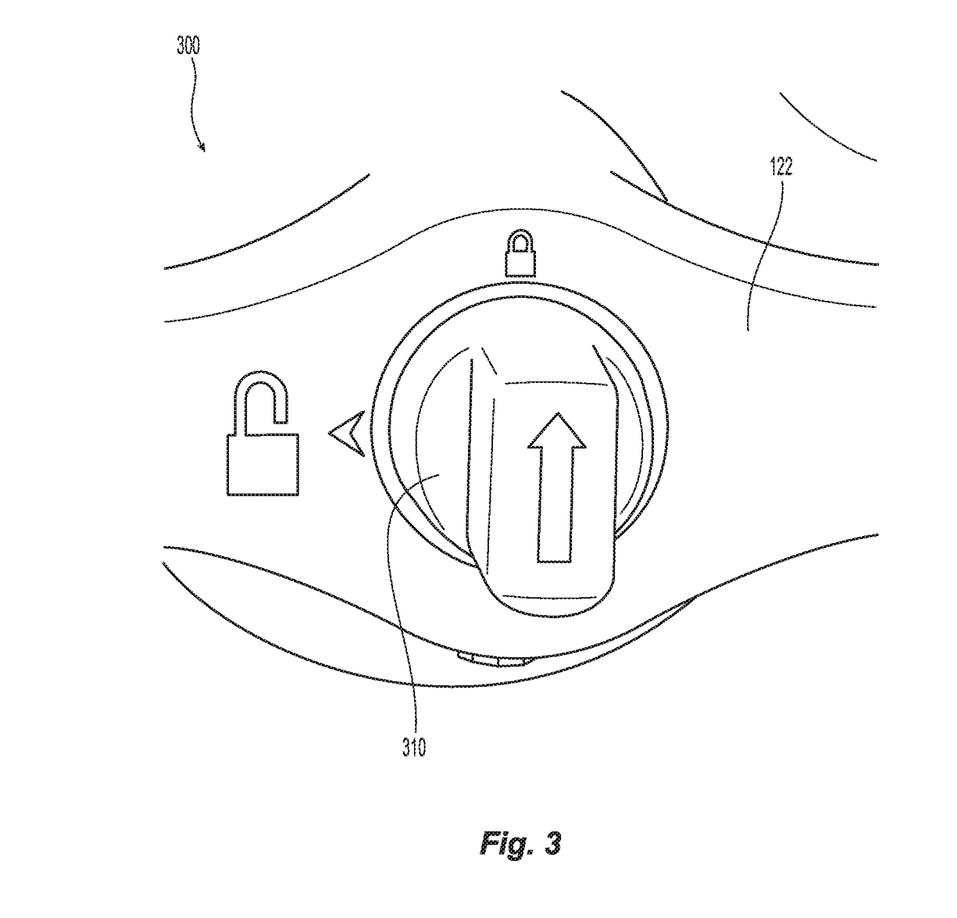
FIG. 3 is a perspective view of a proximal portion of a bag locking mechanism of the specimen containment device of FIGS. 1A and 2 shown in a locked position.

Referring initially to FIGS. 1A, 1B and 2, a specimen containment device is shown and is referred to as device 10. Device 10 generally includes an actuation assembly 100, and a bag assembly 200. A bag locking mechanism 300, as shown in FIGS. 3-6, enables actuation assembly 100 to selectively hold or retain bag assembly 200. FIGS. 1A and 1B illustrate actuation assembly 100 holding bag assembly 200, and FIG. 2 illustrates bag assembly 200 released from engagement with actuation assembly 100.

As shown in FIGS. 1A, 1B and 2, actuation assembly 100 includes a handle assembly 120, an elongated member 140 extending distally from handle assembly 120 and defining a longitudinal axis "A-A," a release rod 160 extending distally from a portion of handle assembly 120 and through elongated member 140, and a holding assembly 180 disposed distally of elongated member 140.

Handle assembly 120 includes a first, proximal handle 122 and a second, distal handle 124. Proximal handle 122 is movable along the longitudinal axis "A-A" relative to distal handle 124 and relative to elongated member 140. A proximal portion 162 of release rod 160 is coupled to proximal handle 122, such that longitudinal translation of proximal handle 122 relative to distal handle 124 and relative to elongated member 140 causes a corresponding longitudinal translation of release rod 160.

Holding assembly 180 includes a first arm 182 and a second arm 184. Both first arm 182 and second arm 184 are curved or arcuate, and extend distally from and/or are coupled to a distal portion 164 of release rod 160. Additionally, portions of release rod 160, first arm 182 and/or second arm 184 may be made from a shape memory material to help maintain a respective shape thereof after travelling at least partially through elongated member 140 or after being articulated (FIG. 1B).

Figure 4:
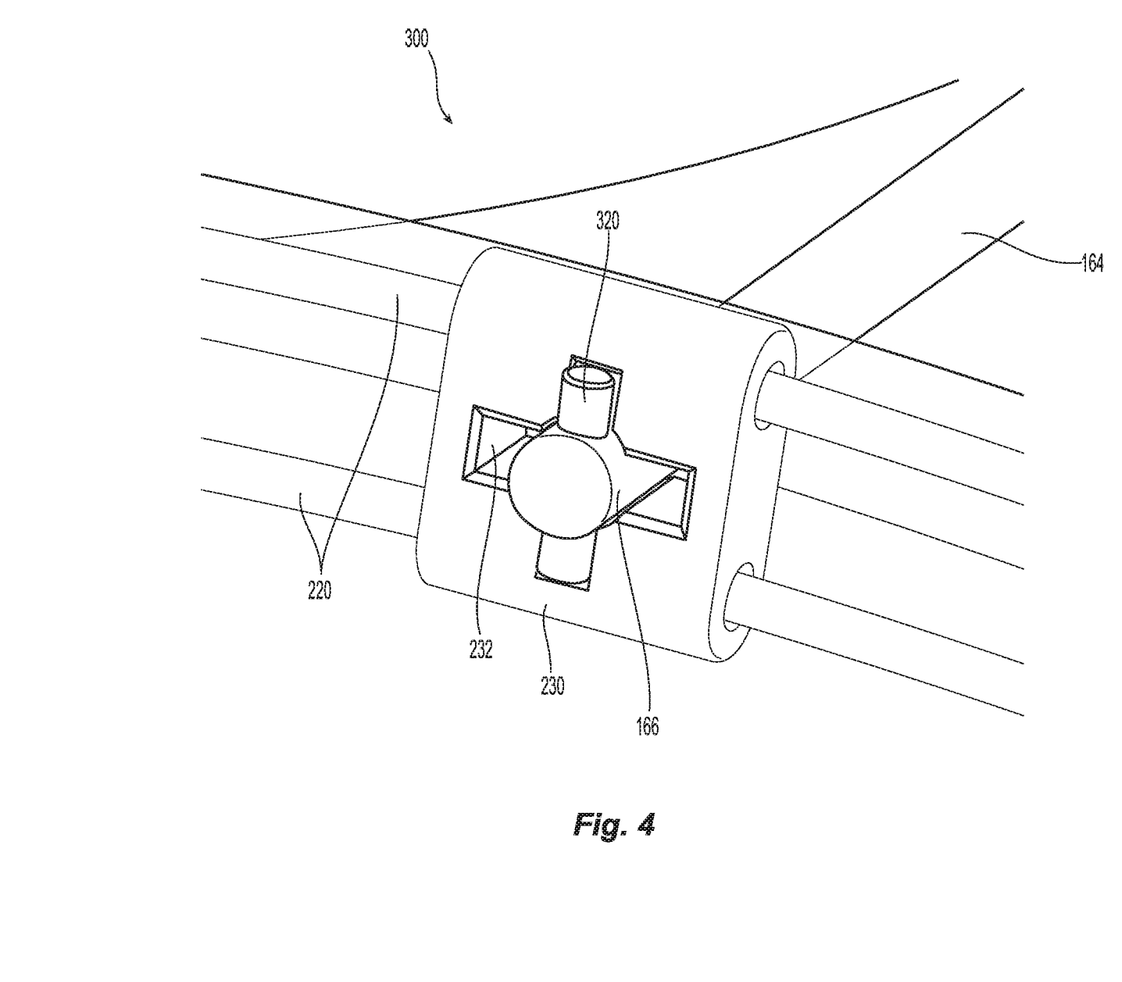
FIG. 4 is a perspective view of a distal portion of the bag locking mechanism of the specimen containment device of FIGS. 1A and 2 shown in a locked position.
Figure 6:
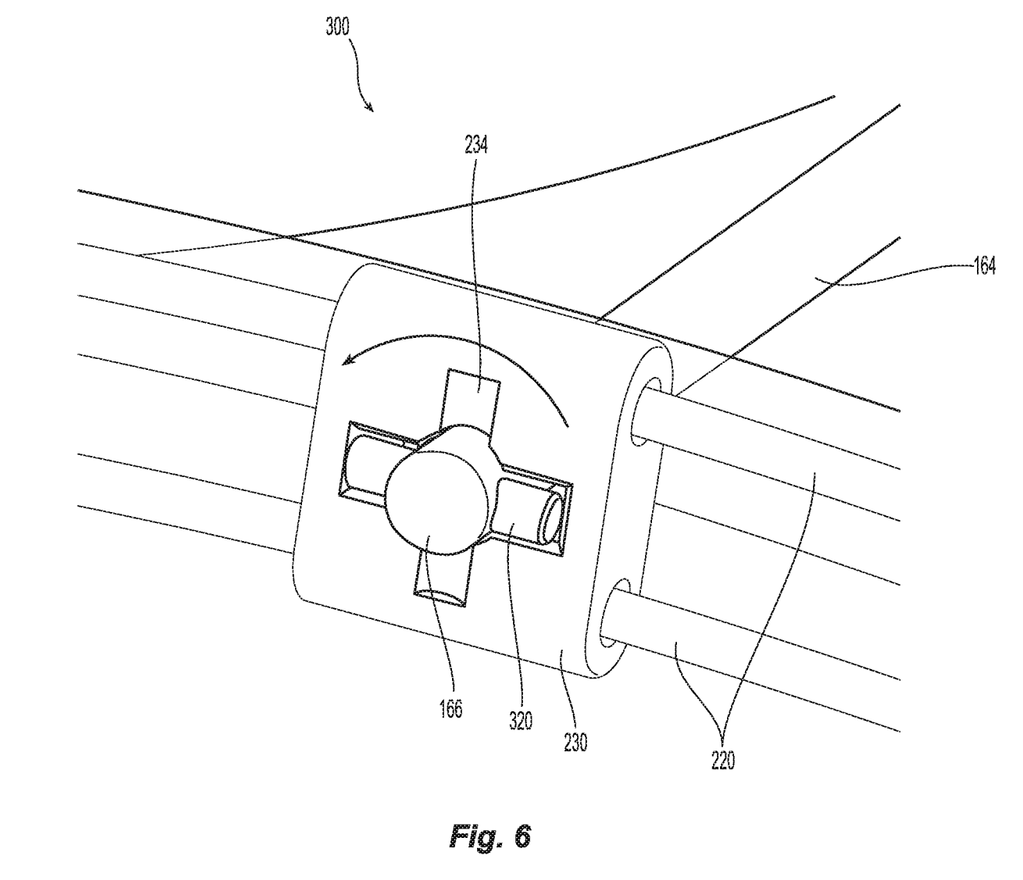
FIG. 6 is a perspective view of a distal portion of the bag locking mechanism of the specimen containment device of FIGS. 1A and 2 shown in the unlocked position.
Figure 7:
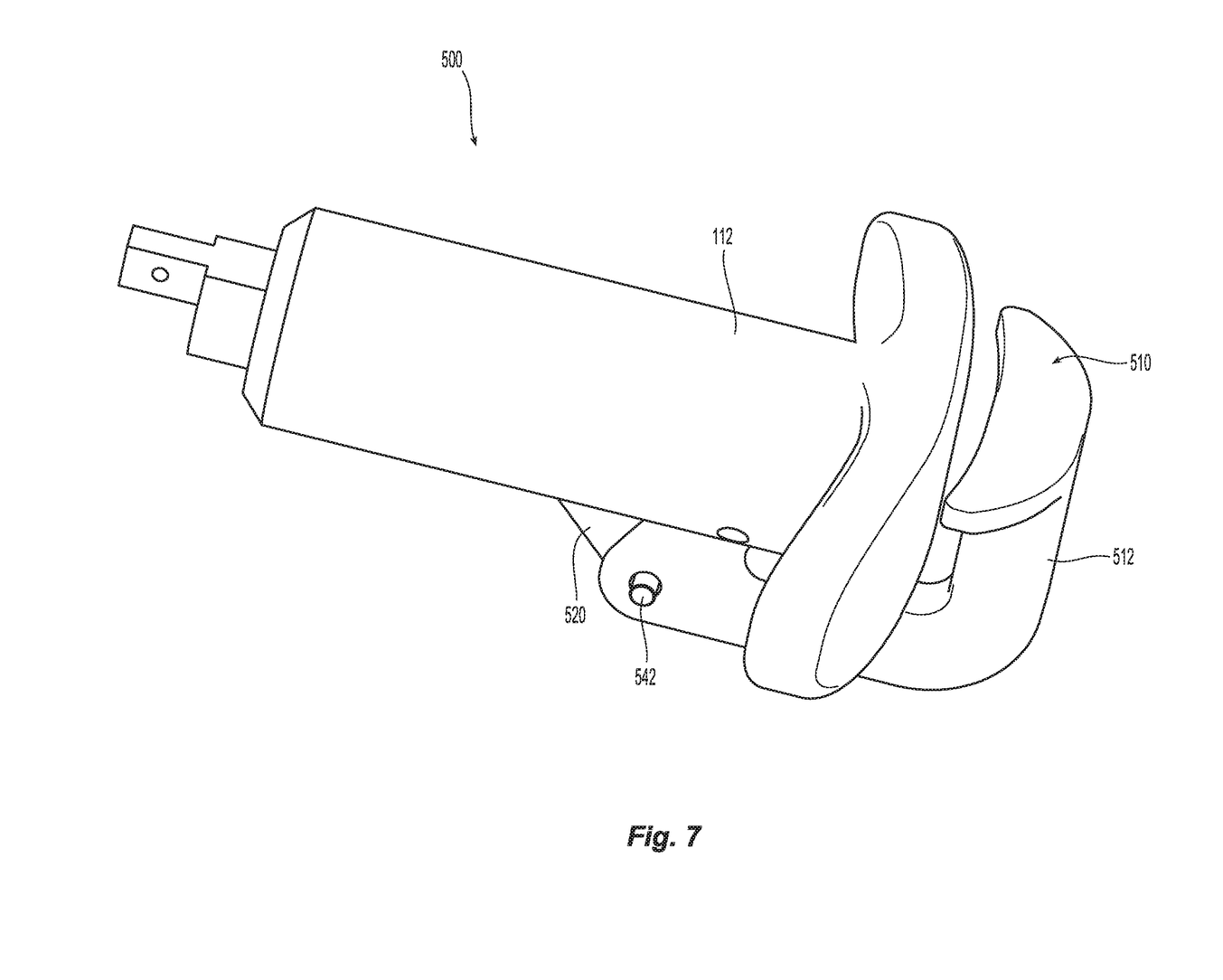
FIGS. 7 and 8 are perspective views of portions of a handle assembly of the specimen containment device of FIGS. 1A-6 including an articulation locking mechanism in an unlocked orientation.
Figure 8:
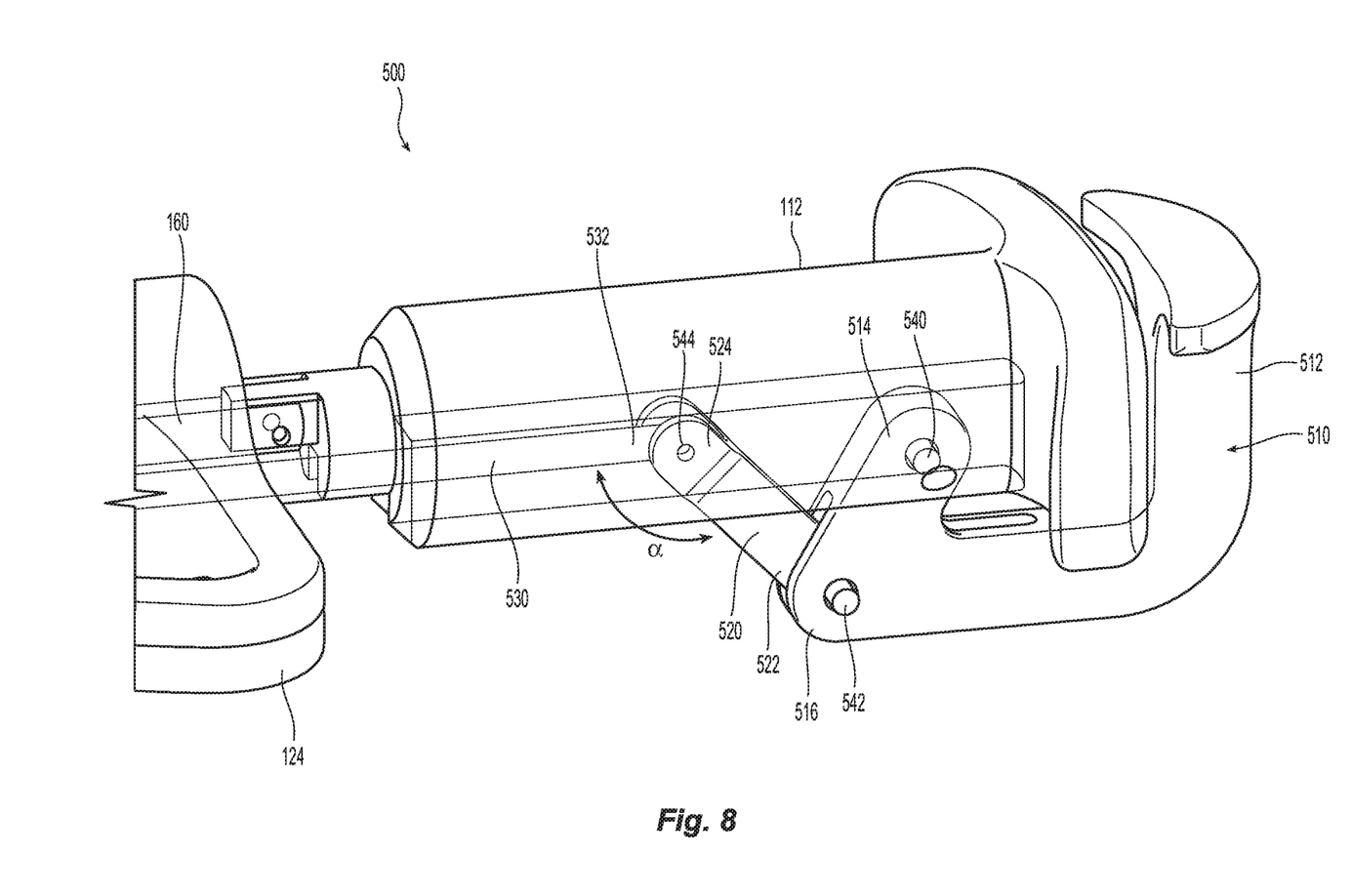

With continued reference to FIGS. 1A, 1B and 2, bag assembly 200 includes a bag 210, a rim 220, and at least one securing structure 230. Bag 210 may be made of any suitable material, including a porous material, and may include at least one filter. Rim 220 is made of a sufficiently flexible material such that bag assembly 200 including rim 220 is retractable through elongated member 140. Rim 220 may be made of a nickel-titanium alloy, such as Nitinol. Further, rim 220 may include more than one rim or wire at least partially encircling an opening of bag 210. For example, FIGS. 4 and 6 illustrate rim 220 including two wires, and illustrate rim 220 extending through securing structure 230. Securing structure 230 includes an opening (e.g., a rectangular opening) 232 (FIG. 4) defined therein and extending longitudinally therethrough, and a receptacle (e.g., a rectangular receptacle) 234 extending partially therethrough.

Referring now to FIGS. 3-6, bag locking mechanism 300 is shown. Bag locking mechanism 300 is engaged with release rod 160 and is configured to selectively engage bag assembly 200. More particularly, bag locking mechanism 300 includes a proximal portion or knob 310 (FIGS. 3 and 5), and a distal portion or finger 320. Proximal portion 310 of bag locking mechanism 300 is engaged with or coupled to proximal portion 162 of release rod 160, and extends proximally through proximal handle 122 of handle assembly 120. Distal portion 320 of bag locking mechanism 300 is engaged with or coupled to or adjacent a distal end 166 of release rod 160. Additionally, distal portion 320 of bag locking mechanism 300 is configured to selectively extend through opening 232 of securing structure 230 of bag assembly 200 (FIG. 6), and to sit at least partially within receptacle 234 of securing structure 230 of bag assembly 200 (FIG. 4).

Figure 5:
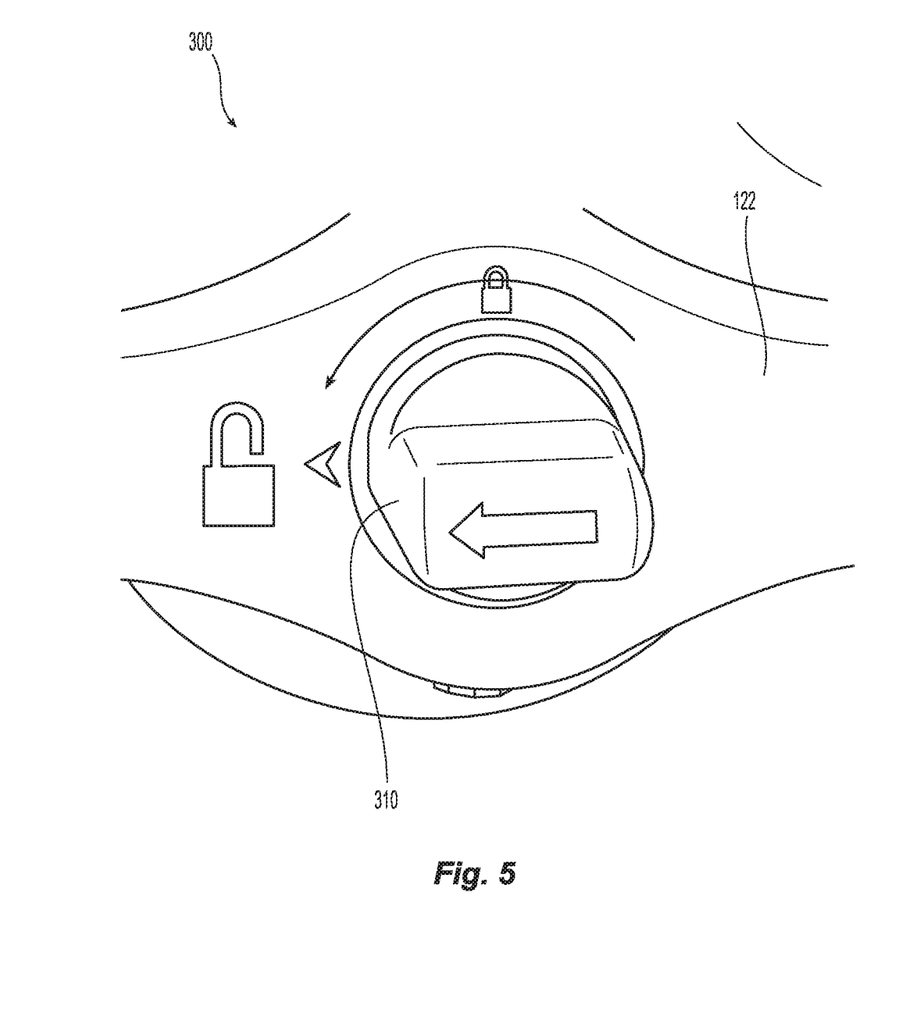
FIG. 5 is a perspective view of a proximal portion of the bag locking mechanism of the specimen containment device of FIGS. 1A and 2 shown in an unlocked position.

Rotation of bag locking mechanism 300 about the longitudinal axis "A-A" relative to elongated member 140, causes bag locking mechanism 300 to move between a locked orientation (FIGS. 3 and 4) and an unlocked orientation (FIGS. 5 and 6). In its locked orientation, distal portion 320 of bag locking mechanism 300 is at least partially disposed within receptacle 234 of securing structure 230 of bag assembly 200, thereby preventing or hindering proximal handle 122 of handle assembly 120 (and thereby release rod 160) from moving proximally relative to elongated member 140, and thereby preventing disengagement of bag assembly 200. In an unlocked orientation, distal portion 320 of bag locking mechanism 300 is aligned with opening 232 of securing structure 230 of bag assembly 200, thereby permitting proximal handle 122 of handle assembly 120 (and thereby release rod 160) to move proximally relative to elongated member 140 and bag assembly 200, which would thereby move release rod 160 out of engagement with bag assembly 200.

In use, a predetermined amount of proximal translation of proximal handle 122, and thus release rod 160, relative to elongated member 140 causes holding assembly 180 and bag assembly 200 (when bag assembly 200 is engaged with release rod 160), to be moved at least partially through (e.g., all the way through) elongated member 140. When removal of a specimen is desired, bag locking mechanism 300 can remain in the locked configuration, thereby permitting removal of bag assembly 200 (e.g., with specimen within bag 210) from the body (e.g., at least partially through elongated member 140). Removing actuation assembly 100 from patient while leaving bag assembly 200 within the patient, is permitted by positioning bag locking mechanism 300 in the unlocked orientation.

Referring now to FIGS. 1A, 1B and 7-10, an articulation locking mechanism 500 is shown. Articulation locking mechanism 500 is configured to lock holding assembly 180 in a straight, or non-articulated position relative to elongated member 140 of actuation assembly 100 (FIG. 1A). FIG. 1B shows holding assembly 180 in an angled or articulated position relative to elongated member 140. While all of the components of bag locking mechanism 300 may not be explicitly shown in FIGS. 7-10 (for clarity), articulation locking mechanism 500 is usable with bag locking mechanism 300.

With particular reference to FIGS. 7-10, articulation locking mechanism 500 engages proximal handle 122 and extends through distal handle 124 and elongated member 140. In particular, articulation locking mechanism 500 includes an articulation handle 510, a link 520, and an articulation rod 530. A proximal portion 512 of articulation handle 510 is disposed proximally of proximal handle 122, and a second portion 514 of articulation handle 510 is at least disposed within part (e.g., a channel) of proximal handle 122, and a distal portion 516 of articulation handle 510 is disposed distally of proximal portion 512 and distally of second portion 514.

Articulation handle 510 is pivotally connected to proximal handle 122 with a first pin 540. More particularly, first pin 540 pivotally couples second portion 514 of articulation handle 510 to proximal handle 122. A second pin 542 pivotally couples distal portion 516 of articulation handle 510 to a proximal portion 522 of link 520. In the position shown in FIG. 8, link 520 and articulation rod 530 form an angle α, which is within the range of about 100° to about 120°. A third pin 544 pivotally couples a distal portion 524 of link 520 to a proximal portion 532 of articulation rod 530. A distal portion of articulation rod 530 is engaged with a proximal portion 182 of holding assembly 180 (FIGS. 1A, 1B and 2).

Articulation rod 530 is movable between a first, proximal position associated with holding assembly 180 and bag assembly 200 being articulated or disposed at an angle relative to longitudinal axis "A-A" (FIG. 1B), and a second, distal position associated with holding assembly 180 and bag assembly 200 being non-articulated or aligned with longitudinal axis "A-A" (FIG. 1A).

Figure 9:
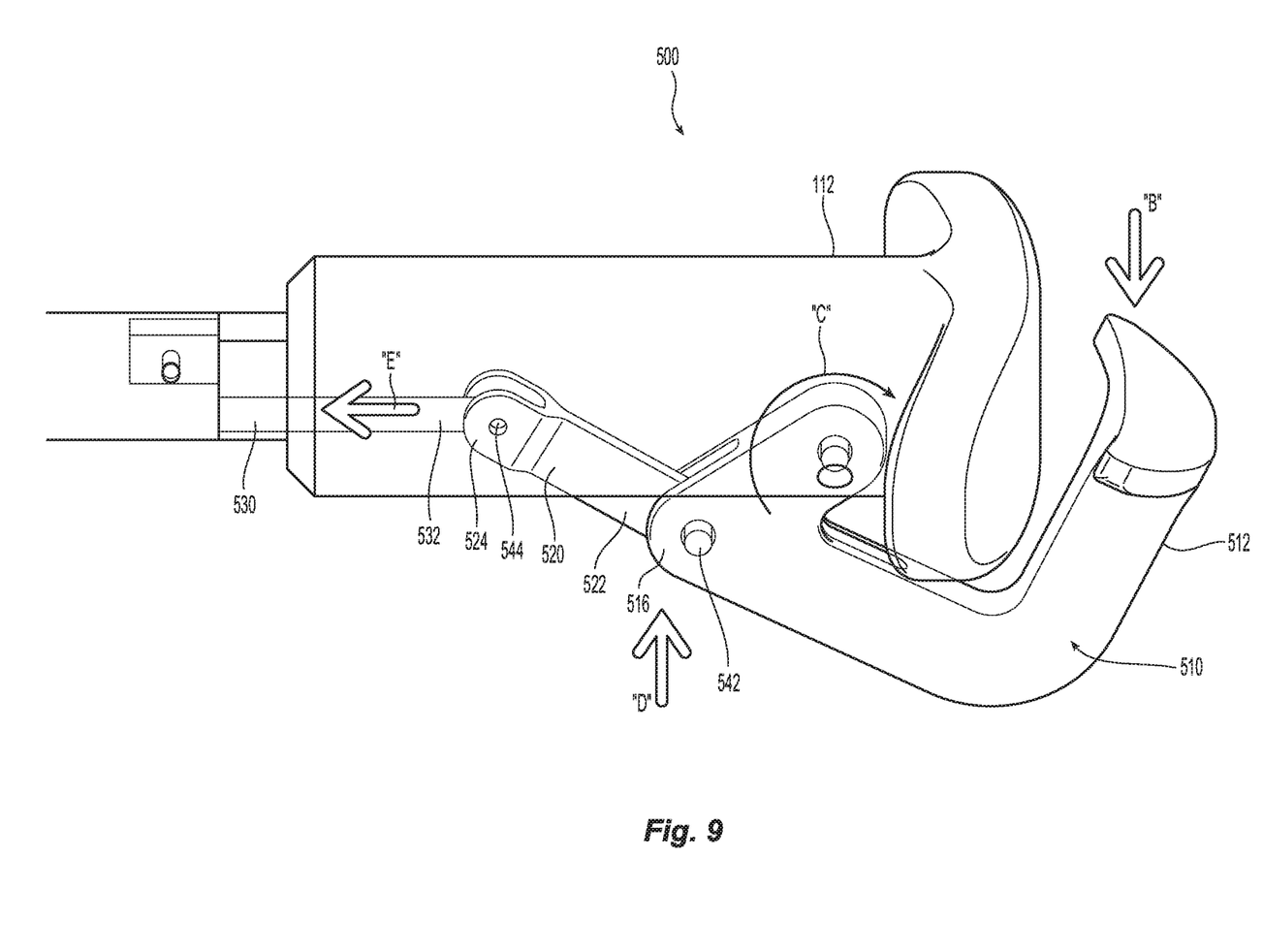
FIG. 9 is a perspective view of the articulation locking mechanism of FIGS. 7-8 between the unlocked orientation and a locked orientation.

To lock bag assembly 200 in the non-articulated position (FIG. 1A), a user actuates or pushes articulation handle 510 of articulation locking mechanism 500 downward in the general direction of arrow "B" in FIG. 9. With continued reference to FIG. 9, as articulation handle 510 of articulation locking mechanism 500 is pushed down or actuated, second portion 514 of articulation handle 510 pivots about first pin 540 relative to proximal handle 122 and rotates in the general direction of arrow "C." This movement also causes distal portion 516 of articulation handle 510, and thus proximal portion 522 of link 520, to move upward in the general direction of arrow "D," thereby causing distal portion 524 of link 520 to move distally in the general direction of arrow "E." The distal movement of distal portion 524 of link 520 causes articulation rod 530 to move distally. A distal portion of articulation rod 530 engages proximal portion 182 of holding assembly 180 (e.g., via a cam and slot arrangement), such that distal movement of articulation rod 530 moves or cams holding assembly 180 (and bag assembly 200, when engaged therewith) into the non-articulated position (FIG. 1A).

Figure 10:
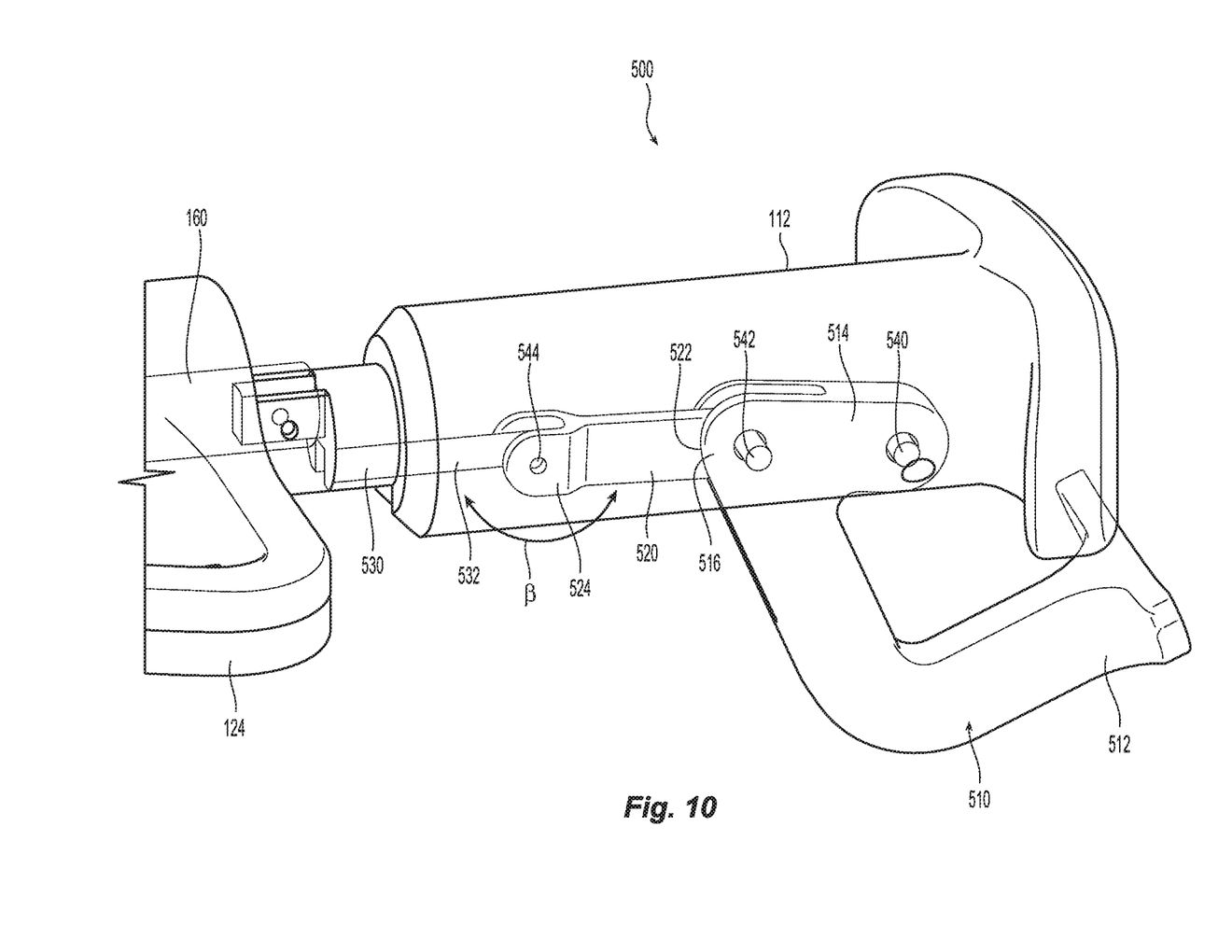
FIG. 10 is a perspective view of the articulation locking mechanism of FIGS. 7-9 in the locked orientation.

With reference to FIG. 10, which corresponds to bag assembly 200 being in its non-articulated position, link 520 and articulation rod 530 form an angle β, which is at least about 180°, e.g., in the range of about 180° to about 220°. This angle β essentially prevents or hinders proximal movement of articulation rod 530 relative to proximal handle 112, since proximal movement of articulation rod 530 would cause binding or upward movement of proximal portion 522 of link 520, which is physically blocked by inside walls of proximal handle 112. As such, when in use, a proximally-directed force (e.g., on holding assembly 180, bag assembly 200 or on a distal portion of articulation rod 530) does not cause holding assembly 180 to move toward the articulated position; movement of holding assembly 180 (and associated bag assembly 200) toward the articulated position may make it difficult for a user (e.g., surgeon) to position or maneuver bag assembly 200 to load a specimen therein.

Further details of a specimen containment device or specimen removal device can be found in commonly owned, U.S. Pat. No. 5,647,372 to Tovey et al. and in U.S. Pat. No. 5,465,731 to Bell et al., the entire contents of each of which are incorporated by reference herein.

From the foregoing and with reference to the various figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A specimen containment device, comprising:
   an actuation assembly including:
      a handle assembly;
         an elongated member extending distally from the handle assembly and defining a longitudinal axis;

a release rod extending distally from a portion of the handle assembly; and a holding assembly disposed distally of the elongated member, at least a portion of the holding assembly movable from a first position where the at least a portion of the holding assembly is disposed along the longitudinal axis, to a second position where the at least a portion of the holding assembly is disposed at a non-parallel angle with respect to the longitudinal axis;

a bag assembly;

a bag locking mechanism disposed in mechanical cooperation with the handle assembly of the actuation assembly and configured to enable the actuation assembly to selectively retain the bag assembly, wherein the bag locking mechanism includes:

a proximal portion coupled to a proximal portion of the release rod and extends through a proximal handle of the handle assembly; and a distal portion coupled to a distal end of the release rod and is configured to selectively extend through an opening of a securing structure of the bag assembly, and wherein the distal portion is disposed at a non-parallel angle relative to the longitudinal axis; and an articulation locking assembly disposed in mechanical cooperation with the handle assembly of the actuation assembly and configured to selectively lock the holding assembly in the first position.

2. The specimen containment device according to claim 1, wherein the holding assembly includes a first arm and a second arm which are each disposed arcuately relative to the longitudinal axis.

3. The specimen containment device according to claim 2, wherein both of the first arm and the second arm are longitudinally translatable at least partially through the elongated member.

4. The specimen containment device according to claim 2, wherein both the first arm and the second arm are made from a shape memory material.

5. The specimen containment device according to claim 1, wherein the handle assembly includes a distal handle, the proximal handle translatable along the longitudinal axis relative to the distal handle.

6. The specimen containment device according to claim 5, wherein the proximal portion of the release rod is coupled to the proximal handle such that longitudinal translation of the proximal handle relative to the distal handle causes corresponding longitudinal translation of the release rod.

7. The specimen containment device according to claim 5, wherein the articulation locking mechanism includes an articulation handle disposed proximally of the proximal handle of the handle assembly, an articulation rod engaged with a proximal portion of the holding assembly, and a link interconnecting the articulation handle and the articulation rod.

8. The specimen containment device according to claim 7, wherein the articulation handle is pivotally connected to the proximal handle of the handle assembly and is movable relative to the proximal handle between a first position where the articulation rod is longitudinally translatable relative to the elongated member, and a second position where the articulation rod is fixed from moving longitudinally relative to the elongated member.

9. The specimen containment device according to claim 8, wherein when the articulation handle is in the first position, the link and the articulation rod form an angle in the range of about 100° to about 120°.

10. The specimen containment device according to claim 9, wherein when the articulation handle is in the second position, the link and the articulation rod form an angle of at least 180°.

11. The specimen containment device according to claim 9, wherein when the articulation handle is in the second position, the link and the articulation rod form an angle in the range of about 180° to about 220°.

12. The specimen containment device according to claim 7, wherein the link is pinned to the articulation handle with a first pin, and wherein the link is pinned to the articulation rod with a second pin.

13. The specimen containment device according to claim 1, wherein the distal portion of the bag locking mechanism is configured to selectively sit at least partially within a receptacle of the securing structure of the bag assembly.

14. The specimen containment device according to claim 13, wherein rotation of at least a portion of the bag locking mechanism about the longitudinal axis relative to the elongated member causes the distal portion of the bag locking mechanism to move from a first orientation where the distal portion of the bag locking mechanism is at least partially within the receptacle of the securing structure, to a second orientation where the distal portion of the bag locking mechanism is aligned with the opening of the securing structure.

15. A specimen containment device, comprising:

an actuation assembly including:

a handle assembly including a proximal handle and a distal handle, the proximal handle translatable along a longitudinal axis relative to the distal handle;

an elongated member extending distally from the handle assembly and defining the longitudinal axis;

a release rod extending distally from a portion of the handle assembly; and a holding assembly disposed distally of the elongated member, at least a portion of the holding assembly movable from a first position where the at least a portion of the holding assembly is disposed along the longitudinal axis, to a second position where the at least a portion of the holding assembly is disposed at a non-parallel angle with respect to the longitudinal axis;

a bag assembly;

a bag locking mechanism disposed in mechanical cooperation with the handle assembly of the actuation assembly and configured to enable the actuation assembly to selectively retain the bag assembly; and an articulation locking assembly disposed in mechanical cooperation with the handle assembly of the articulation assembly and configured to selectively lock the holding assembly in the first position, wherein the articulation locking mechanism includes an articulation handle disposed proximally of the proximal handle of the handle assembly, an articulation rod engaged with a proximal portion of the holding assembly, and a link interconnecting the articulation handle and the articulation rod.

16. The specimen containment device according to claim 15, wherein the link is pinned to the articulation handle with a first pin, and wherein the link is pinned to the articulation rod with a second pin.

* * * * *